(12) United States Patent
Torrie (10) Patent No.: US 9,968,365 B2
(45) Date of Patent: *May 15, 2018

(54) STABILIZING MICROFRACTURE DEVICE

(71) Applicant: Smith & Nephew, Inc., Memphis, TN (US)

(72) Inventor: Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 113 days.

This patent is subject to a terminal disclaimer.

(21) Appl. No.: 15/218,645

(22) Filed: Jul. 25, 2016

(65) Prior Publication Data

US 2017/0128080 A1    May 11, 2017

Related U.S. Application Data

(63) Continuation of application No. 13/982,434, filed as application No. PCT/US2012/022941 on Jan. 27, 2012, now Pat. No. 9,398,918.

(60) Provisional application No. 61/436,653, filed on Jan. 27, 2011.

(51) Int. Cl.
*A61B 17/16* (2006.01)
*A61B 17/34* (2006.01)

(52) U.S. Cl.
CPC ...... *A61B 17/1604* (2013.01); *A61B 17/1664* (2013.01); *A61B 17/1666* (2013.01); *A61B 17/1668* (2013.01); *A61B 17/3472* (2013.01)

(58) Field of Classification Search
CPC ............ A61B 17/1604; A61B 17/1664; A61B 17/1666; A61B 17/1668; A61B 17/3472
See application file for complete search history.

(56) References Cited

U.S. PATENT DOCUMENTS

| | | |
|---|---|---|
| 4,239,045 A | 12/1980 | Schlein |
| 4,583,270 A | 4/1986 | Kenna |
| 5,713,906 A | 2/1998 | Grothues-Spork et al. |
| 6,764,491 B2 | 7/2004 | Frey et al. |
| 8,840,622 B1 | 9/2014 | Vellido et al. |
| 9,398,918 B2 * | 7/2016 | Torrie ................ A61B 17/1604 |
| 2004/0147932 A1 | 7/2004 | Burkinshaw et al. |

(Continued)

FOREIGN PATENT DOCUMENTS

| | | |
|---|---|---|
| WO | 2007106895 A2 | 9/2007 |
| WO | 2008045902 A2 | 4/2008 |

OTHER PUBLICATIONS

Patent Examination Report No. 1 for related Australian Application No. 2012211188 dated Jul. 14, 2015.

(Continued)

*Primary Examiner* — Larry E Waggle, Jr.

(74) *Attorney, Agent, or Firm* — Burns & Levinson, LLP; Joseph M. Maraia (57) ABSTRACT

A microfracture device comprising a guide shaft having a proximal end and a distal end and defining an internal passage between the proximal and distal ends, the distal end having a curved tip, a stabilizing portion disposed along an outer surface of the guide shaft, at least a portion of the stabilizing portion being wider than the guide shaft, and a flexible element movably positioned within the internal passage of the guide shaft, the flexible element having a distal tip configured for driving into bone.

15 Claims, 13 Drawing Sheets

(56) References Cited

U.S. PATENT DOCUMENTS

| | | |
|---|---|---|
| 2007/0270870 A1 | 11/2007 | Torrie et al. |
| 2009/0143782 A1 | 6/2009 | Levi |
| 2010/0191195 A1 | 7/2010 | Kirschenbaum |
| 2010/0249786 A1 | 9/2010 | Schmieding et al. |
| 2010/0331851 A1 | 12/2010 | Huene |
| 2010/0331897 A1 | 12/2010 | Linder |
| 2012/0071876 A1 | 3/2012 | Stoll et al. |
| 2012/0290020 A1 | 11/2012 | Meridew et al. |
| 2013/0053904 A1 | 2/2013 | Penenberg |

OTHER PUBLICATIONS

Office Action from related European Application No. 12702159.0-1654 dated May 27, 2016.
International Search Report from Application No. PCT/US2014/022537 dated May 27, 2014.

* cited by examiner

STABILIZING MICROFRACTURE DEVICE

CROSS-REFERENCE TO RELATED APPLICATION

This application claims priority to and the full benefit of U.S. Provisional Application Ser. No. 61/436,653, filed Jan. 27, 2011, and titled "Stabilizing Manual Hip Microfracture," the entire contents of which is incorporated herein by reference.

FIELD

This document relates to a device for performing a microfracture procedure.

BACKGROUND

Articulating body joints are surfaced with hyaline cartilage, which is a very durable low coefficient of friction natural material. These surfaces are often damaged when subjected to high repeated loading, such as when one runs. This is particularly true for lower body compressive joints such as the ankle, knee, hip and spine.

Resurfacing of the cartilage surfaces is a large area of study in the orthopaedic industry. One technique used for resurfacing of the cartilage is referred to as microfracture. Rather than replacing the damaged articular cartilage with an artificial implant, microfracture stimulates the body to replace the surface with a fibrous cartilage. Fibrocartilage is not as robust and does not have the low coefficient of friction that hyaline cartilage does, but it does provide patients with reduced pain and enables them to participate in an active lifestyle.

Microfracture procedures are generally performed by first removing the damaged layer of cartilage. The damaged layer can vary from about 1 to about 6 mm in thickness. A sharp microfracture pick is then driven about 2 to about 5 mm through the underlying subchondral bone to a blood supply. When the pick is removed, a small channel remains. A series of channels can be formed in the subchondral bone such that blood travels along the channel and clots in the area of the removed cartilage.

SUMMARY

In a general aspect, a microfracture device includes a guide shaft having a proximal end and a distal end and defining an internal passage between the proximal and distal ends, the distal end having a curved tip, a stabilizing portion disposed along an outer surface of the guide shaft, at least a portion of the stabilizing portion being wider than the guide shaft, and a flexible element movably positioned within the internal passage of the guide shaft, the flexible element having a distal tip configured for driving into bone.

Implementations may include one or more of the following features. The device further includes a handle operatively coupled to the proximal end of the guide shaft. The handle defines a passageway configured to receive a portion of the flexible element therethrough. The handle is operatively coupled to the proximal end of the guide shaft such that the guide shaft can be translated proximally and distally relative to the stabilizing portion and rotated relative to the stabilizing portion. The guide shaft includes at least one angled tip at the distal end of the guide shaft. The stabilizing portion includes a body defining an internal passage that receives a portion of the guide shaft therethrough. A portion of the body includes a substantially flat outer surface. A portion of the body comprises a substantially curved outer surface. The body defines a longitudinally extending slit that permits the guide shaft to be disposed in and removed from the internal passage of the body. The stabilizing portion includes a flexible body having at least one substantially curved outer surface. The flexible element includes a proximal end that is operatively configured to permit translation of the flexible element proximally and distally through the internal passage of the guide shaft. The proximal end of the flexible element is further operatively configured to permit rotation of the flexible element within the internal passage of the guide shaft. The flexible element includes a flexible wire. The stabilizing portion includes a recessed portion for receiving a portion of the curved tip of the distal end of the guide shaft.

In another general aspect, a surgical device includes a guide shaft having a proximal end and a distal end, the guide shaft defining an internal passage between the proximal and distal ends and having an angled tip at the distal end of the guide shaft, a support portion disposed about an outer surface of the guide shaft, at least a portion of the support portion being wider than the guide shaft, a handle operatively coupled to the proximal end of the guide shaft, the handle defining an internal passage, and a flexible element having a proximal and a distal end, the flexible element movably positioned within the internal passage of the guide shaft and the internal passage of the handle, the flexible element having an angled distal tip at the distal end of the flexible element.

Implementations may include one or more of the following features. The support portion includes a body defining an internal passage that receives a portion of the guide shaft therethrough. A portion of the body includes a substantially flat outer surface. The stabilizing portion includes a flexible body having at least one substantially curved outer surface.

In another general aspect, a method of performing a microfracture procedure includes positioning a surgical device having a guide shaft with a proximal end and a distal end and an angled tip at the distal end and a stabilizing portion disposed along an outer surface of the guide shaft proximate to a first bone surface such that an outer surface of the stabilizing portion is positioned against a portion of the first bone surface, locating the angled tip of the guide shaft at a desired point of stimulation, driving an angled tip of a flexible element through the guide shaft and into a second bone surface, and removing the flexible element.

Implementations may include one or more of the following features. The method further includes engaging the angled tip of the guide shaft into the second bone surface. The flexible element includes a flexible wire, and wherein driving the angled tip of the flexible wire comprises striking a proximal end of the flexible wire to translate the flexible wire relative to the guide shaft. The flexible element includes a flexible wire, and wherein driving the angled tip of the flexible wire comprising rotating a proximal end of the flexible wire to rotate the flexible wire relative to the guide shaft. The first bone surface includes a portion of a femoral head and the second bone surface includes a portion of the acetabulum. The stabilizing portion includes an outer surface having one of a substantially flat portion or a substantially curved portion and the positioning step includes positioning one of the substantially flat or curved portions against the portion of the femoral head. The positioning step includes the step of inserting at least a portion of the surgical device into an arthroscopic cannula.

The details of one or more implementations are set forth in the accompanying drawings and the description below. Other features, aspects, and advantages will become apparent from the description, the drawings, and the claims.

DETAILED DESCRIPTION

This document describes examples of microfracture devices that can be used during a microfracture procedure to create channels or holes in subchondral bone, for example, to stimulate the production of fibrocartilage between an acetabular cup and a femoral head.

Figure 1A:
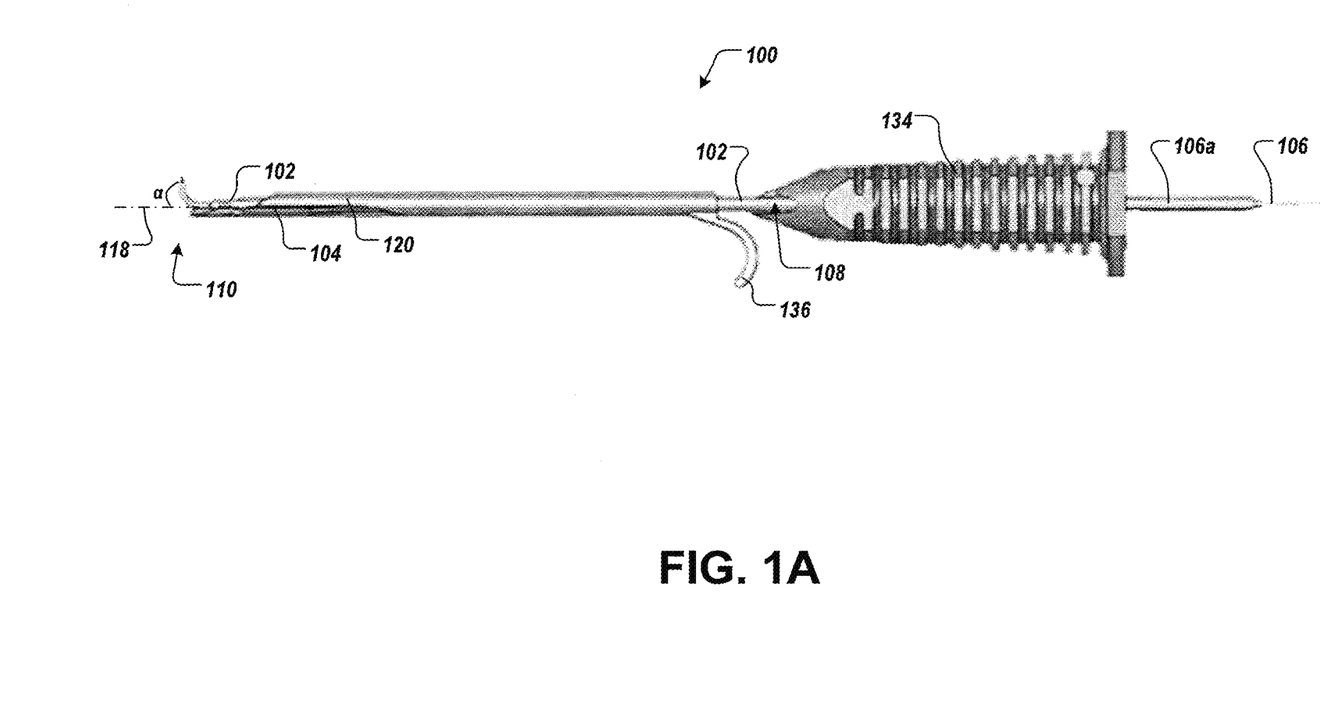
FIG. 1A is a side view of a microfracture device.

Referring to FIG. 1A, a microfracture device 100 includes a guide shaft 102, a stabilizing portion 104, and a flexible element 106, which can be used to create holes or channels in, for example, subchondral bone tissue. The guide shaft 102 has a proximal end 108 and a distal end 110, and can be cannulated such that a lumen or internal passage (not shown) is disposed axially along its length. The flexible element 106, for example, a flexible wire, can be positioned within the internal passage such that proximal and distal ends of the flexible element 106 extend, respectively, beyond the proximal and distal ends 108, 110 of the guide shaft 102. The flexible element 106 can be made from stainless steel, Nitinol, and/or other materials suitable for creating microfracture channels in subchondral bone. The flexible element 106 can include a widened or thickened portion 106a that helps to limit the flexible element 106 from buckling when compressed. At least a part of the outer surface of the stabilizing portion 104 is configured or adapted to contact a portion of a bone surface, such as a contoured surface of the femoral head (not shown), and can help stabilize the microfracture device 100 during microfracture surgery as described further below.

Figure 1B:
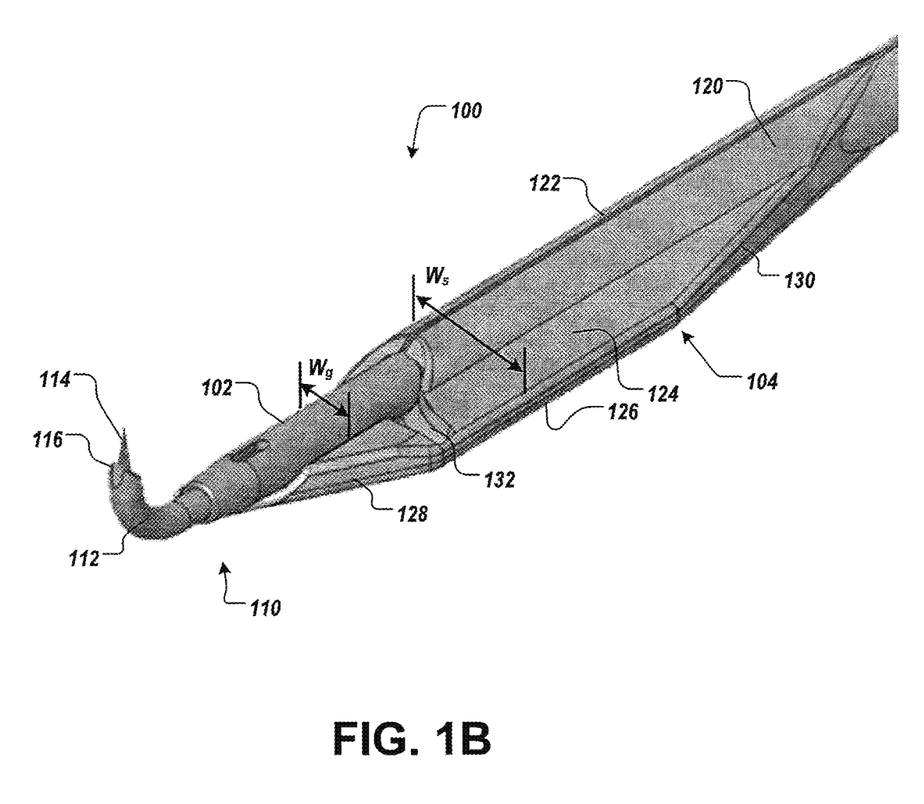
FIG. 1B is a partial perspective view of the microfracture device of FIG. 1A.

Referring also to FIG. 1B, the guide shaft 102 of the microfracture device 100 can be a generally cylindrical structure having a one-piece construction, or the guide shaft 102 can be made of multiple components that are attached to each other via, for example, welding or a press fit engagement. The guide shaft 102 can be made from any biocompatible material including polymers, metals, ceramics, or combinations thereof. The distal end 110 of the guide shaft 102 includes a curved tip region 112 that can guide the flexible element 106 to a selected position and orientation with respect to a microfracture surgery site. For example, referring to FIGS. 1A and 1B, a sharpened distal tip 114 of the flexible element 106, which exits the guide shaft 102 through an opening (not shown) in a distal tip 116 of the guide shaft 102, can form an angle α with respect to a shaft axis 118 such that a transverse channel can be formed into the subchondral bone of, for example, the acetabular cup. The angle α can be between about 20 degrees to about 90 degrees. In some cases, the angle α can be greater than 90 degrees such that the tip 114 of the flexible element 106 points towards the proximal end 108 of the guide shaft 102. The curved tip region 112 can be an integral portion of the guide shaft 102 or can be separately attached to the guide shaft 102. In some cases, the curvature of the curved tip region 112 can be adjusted by the surgeon such that the angle α can be changed as required by the particular microfracture procedure.

Referring to FIG. 1B, the stabilizing portion 104 includes a body 120. A portion of the body 120 can receive the guide shaft 102. For example, an internal passage (not shown) through the body 120 can receive at least a portion of the guide shaft 102. In some cases, the stabilizing portion 104 can be slipped over the guide shaft 102 and adjustably positioned at a particular location along the guide shaft 102. Additionally, the body 120 can define a slit 122 along the stabilizing portion 104 such that the guide shaft 102 can be disposed in and removed from the internal passage (not shown) through the slit 122. In some implementations, the stabilizing portion 104 can be insert-molded around the guide shaft 102. In other implementations, the stabilizing portion 104 can be integrally formed as part of the guide shaft 102. For example, the guide shaft 102 and the stabilizing portion 104 can be formed together in a single machining or molding step. Alternatively, or additionally, various attachment procedures, such as welding or the use of adhesives, may be used to attach the stabilizing portion 104 to the guide shaft 102.

The body 120 of the stabilizing portion 104 includes a wide portion 124 having a generally trapezoidal shape as best seen in FIG. 1B. The wide portion 124 can include other geometries, such as a semicircle or a rectangle, and can extend laterally beyond one or both sides of the body 120. Additionally, the wide portion 124, which can be integrally formed with or separately attached to the body 120, includes an outer surface 126 for contacting a bone surface, such as a surface of a femoral head (FIG. 2A) and/or a hip capsule 700 as shown with reference to FIGS. 7A and 7B. The outer surface 126 generally has a width $W_s$ that is greater than a width $W_g$ or diameter of the guide shaft 102. In some cases, the width $W_s$ can be approximately twice as large as the width $W_g$. The increased width $W_s$ of the outer surface 126 can help distribute forces applied to the contacting bone or soft tissue surface over a larger area, thereby reducing possible damage to the bone surface or, for example, the cartilage overlying the bone surface. All or portions of the outer surface 126 can be substantially flat. In some cases, all or portions of the outer surface 126 can be substantially curved, contoured, or shaped. For example, all or portions of the outer surface 126 can be curved to match or substantially match or conform to a corresponding curvature of a portion of the femoral head as discussed further below. Also, as discussed below, the stabilizing portion 104 can have a leading edge 128, a trailing edge 130, and a recessed portion 132 for improved insertion into and removal from, respectively, a surgical site through, for example, an arthroscopic cannula. The stabilizing portion 104 can be made from any biocompatible material including polymers, elastomers, metals, ceramics, or combinations thereof. Additionally, or alternatively, the stabilizing portion 104 can be made from autoclavable materials such that the stabilizing portion 104 may be reused after surgery. In some cases, the outer surface 126 can include a different surface treatment, surface texture, and/or surface material to minimize slipping while in contact with the bone surface. Alternatively, stabilizing portion 104 can incorporate a soft surface 126 made from an elastomer or balloon to conform to the corresponding curvature of a portion of the femoral head or hip capsule.

Referring again to FIG. 1A, the microfracture device 100 includes a handle 134 that can be coupled to, or formed integral with, the guide shaft 102 near the proximal end 108 to control the movement of the guide shaft 102. Additionally, the stabilizing portion 104 can include a handle portion 136 located at a proximal end of the stabilizing portion. For example, the handle portion 136 can be hook-like structure or other finger-engageable structure that is coupled to a proximal region of the body 120 of the stabilizing portion 104. In use, the user can move, both translationally and rotationally, the handle 134 relative to the handle portion 136, or vice versa, such that the guide shaft 102 moves correspondingly or differently with respect to the stabilizing portion 104. Thus, by manipulating the handle 134 and/or the handle 136, a user can vary the position of the distal tip 114 of the flexible element 106 as well as the distal tip 116 of the guide shaft 102 relative to, for example, the stabilizing portion 104.

Figure 2A:
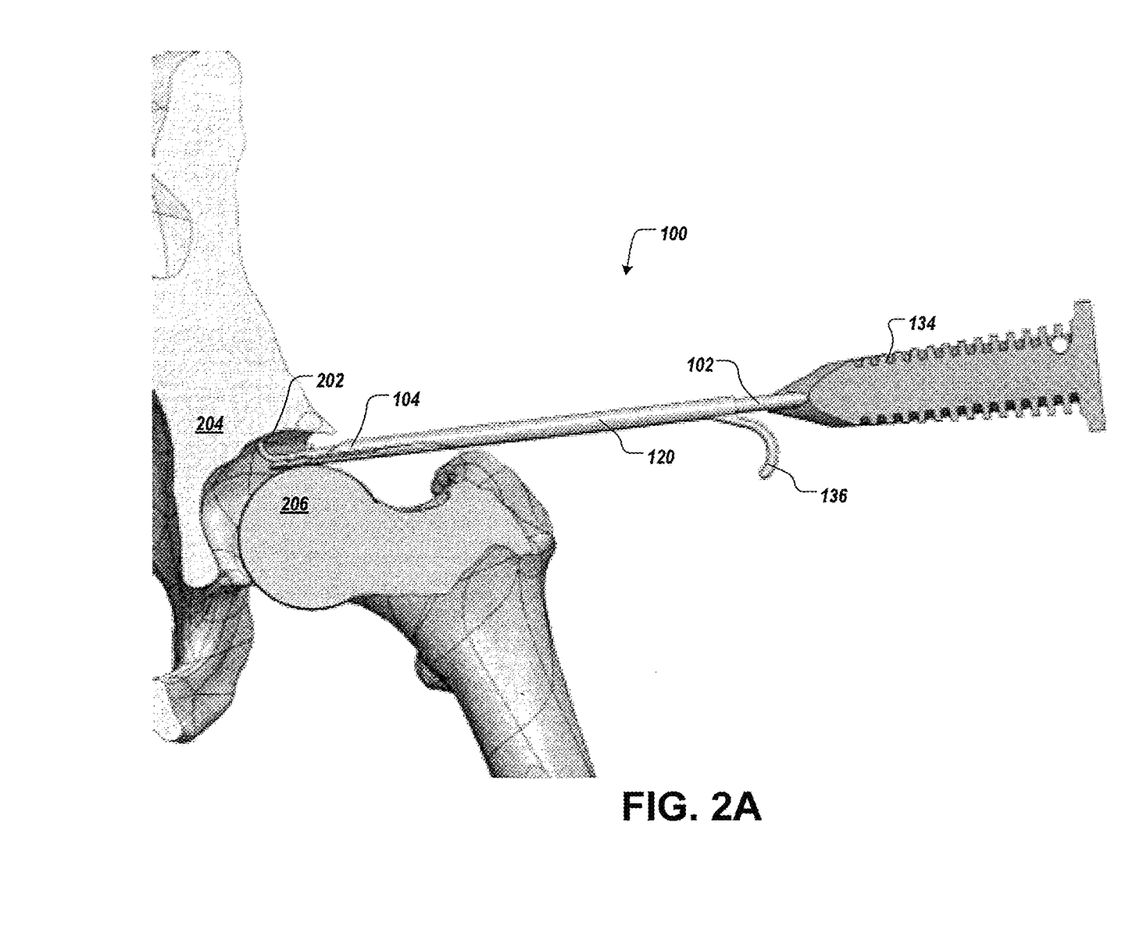
FIGS. 2A-2B illustrate positioning and use of the microfracture device within an acetabular region for performing a microfracture procedure.
Figure 2B:
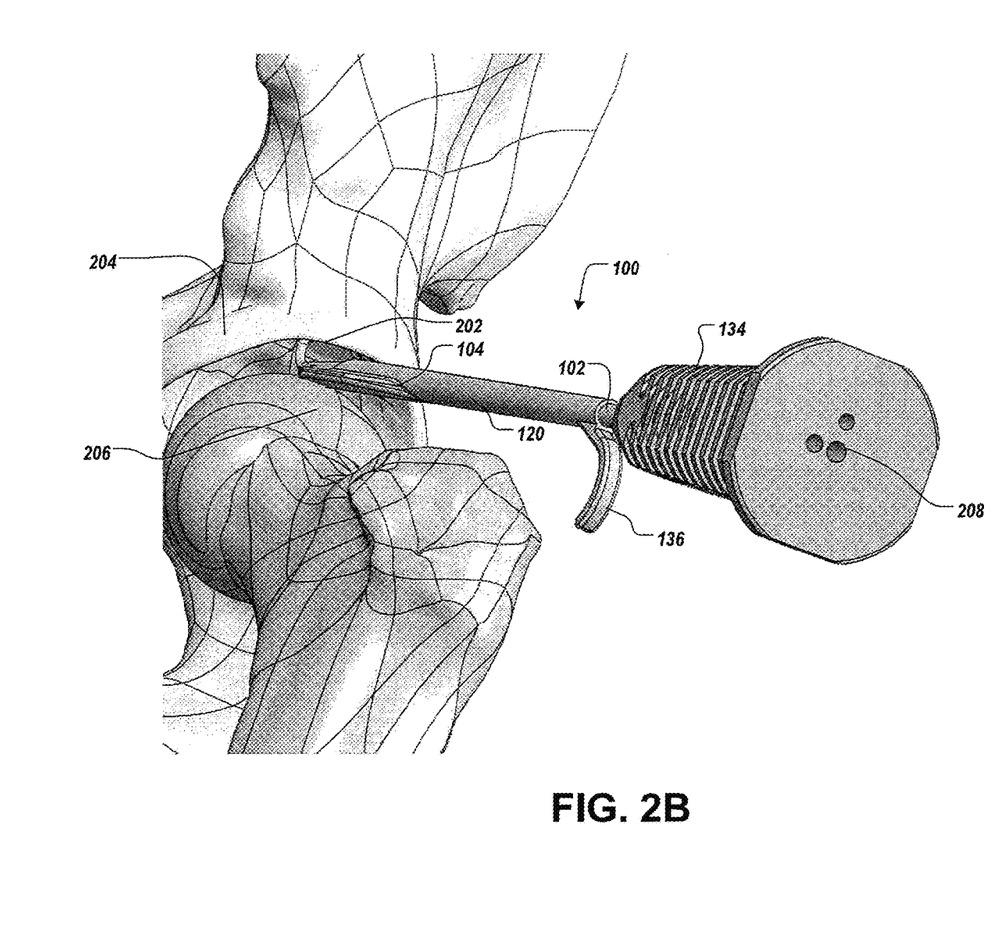

Referring now to FIGS. 2A and 2B, during a microfracture procedure, a user, such as a surgeon inserts the microfracture device 100, for example, through an arthroscopic cannula through a skin of a patient, and positions the device 100 near a microfracture site 202. The microfracture site 202 can be a region where there is breakage in a cartilage layer (not shown) or where a portion of the cartilage layer has been removed and where microfracture may stimulate the growth of fibrocartilage. As shown in FIG. 2A, an exemplary microfracture site 202 is at a desired location on the acetabular cup 204, between the acetabular cup 204 and the femoral head 206. In use, the surgeon can first position the wide portion 124 of the stabilizing portion 104 such that the outer surface 126 of the wide portion 124 contacts an outer surface of the femoral head 206 (FIG. 2A) and/or hip capsule 700 (FIGS. 7A and 7B). Following positioning of the wide portion 124, the surgeon can position the guide shaft 102, for example by manipulating the handle 134, such that the distal tip 116 of the guide shaft 102 contacts an outer surface of the acetabular cup 204 at the microfracture site 202. In some cases, the distal tip 116 of the guide shaft 102 can be partially driven into the bone surface by levering handle 134 around surface 126 of stabilizing portion 104. One or more angled teeth 606 located at the distal end of the guide shaft 102 as described in more detail below with respect to FIG. 6 may augment the ability to drive guide shaft 102 into bone and thus increase the stability of microfracture device 100.

After placing the microfracture device 100 in the selected position relative to the microfracture site 202, the distal tip 114 of the flexible element 106 can be driven through the guide shaft 102 and into the microfracture site 202 to create one or more channels in the subchondral bone. The flexible element 106 may also rotate within the internal passage of the guide shaft 102 and be driven into the subchondral bone with translational and/or rotational movement to create the microfracture channels. For example, a distal tip of the flexible element 106 can be driven into bone by rotating a proximal end of the flexible element 106. The proximal end of the flexible element 106 can exit the guide shaft 102 through an opening (not shown) at the proximal end 108 of the guide shaft 102 and through an opening 208 (FIG. 2B) at a proximal end of the handle 134. A manual rotation device can be attached to the proximal end of the flexible element 106.

In some implementations, the flexible element 106 may be a flexible wire that can translate linearly, i.e. proximally and distally, through the internal passage of the guide shaft 102 to create the microfracture channels. For example, a distal tip of the flexible wire can be driven into bone by striking a proximal end of the flexible wire. The curved shape of the guide shaft 102 helps translate an impact force oriented axially relative to the wire at the proximal end of the wire to a driving force oriented axially relative to the wire at the distal end of the wire. In other words, an impact force at the proximal end of the flexible wire that is oriented in a direction generally parallel to the surface of the microfracture site 202 is transferred to a driving force at the distal end of the flexible wire that is oriented in a direction generally transverse to the surface of the microfracture site 202. The resulting axial impact force at the distal end of the wire allows the distal tip of the flexible wire to be driven into the bone.

During the microfracture procedure steps outlined above, the wide portion 124 of the stabilizing portion 104 can help stabilize and/or minimize unwanted movement of the guide shaft 102 relative to the microfracture site 202. For example, normal and/or friction forces generated between the femoral head 206 and/or hip capsule 700 (FIGS. 7A, 7B) and the outer surface 126 may counteract some of the reaction forces generated at the microfracture site 202 as a result of the rotational or translational drilling process discussed above. Further, the increased surface area of the outer surface 126 can help distribute any forces that may be generated between the stabilizing portion 104 and the femoral head 206 and/or hip capsule 700 (FIGS. 7A, 7B) over a larger area to help minimize damage to, for example, cartilage or bone surfaces of the femoral head 206.

Figure 3A:
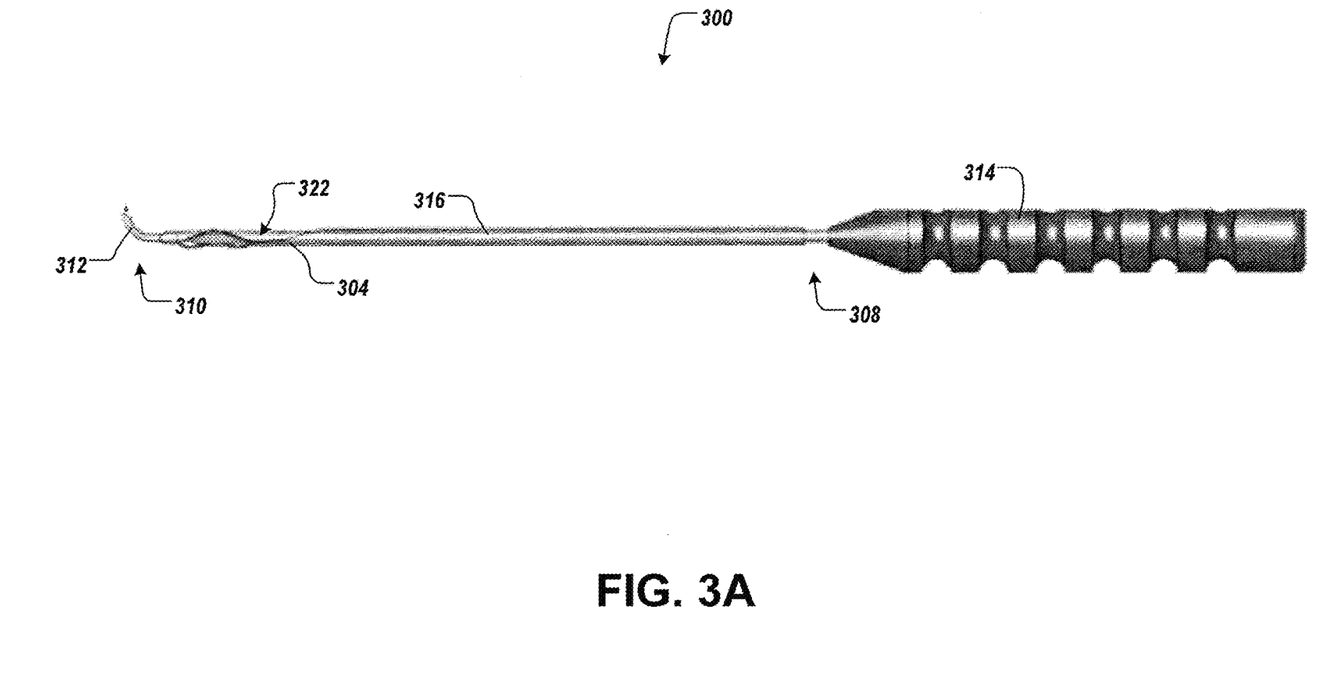
FIG. 3A is a side view of an alternative implementation of a microfracture device.
Figure 3B:
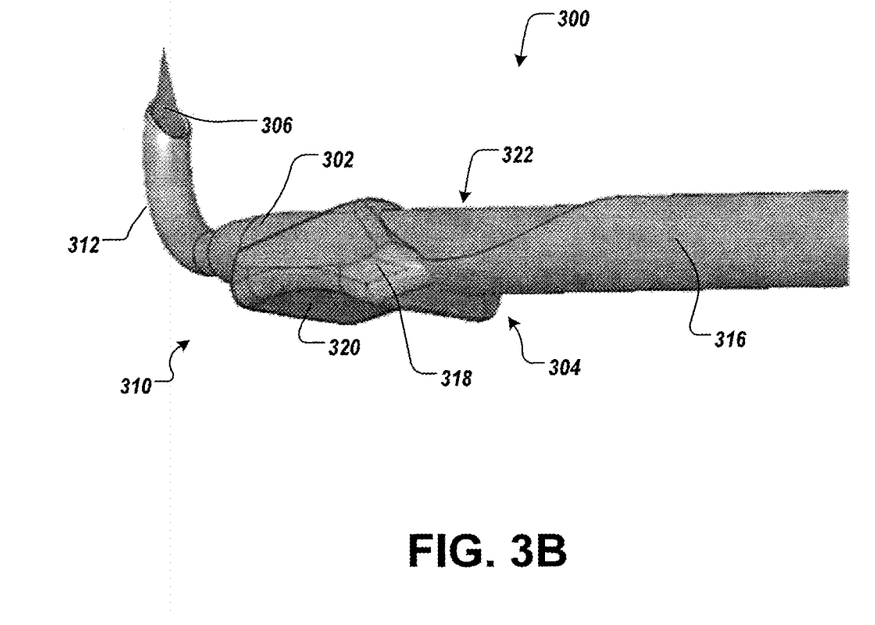
FIG. 3B is a partial perspective view of the microfracture device of FIG. 3A.

Referring to FIGS. 3A and 3B, in an alternative implementation, a microfracture device 300 includes a guide shaft 302, a stabilizing portion 304, and a flexible element 306. The guide shaft 302 has a proximal end 308 and a distal end 310, and can be cannulated such that a lumen or internal passage (not shown) is disposed axially along its length. The flexible element 306, for example, a flexible wire, can be positioned within the internal passage such that flexible element 306 extends both proximally and distally, respectively, beyond the proximal and distal ends 308, 310 of the guide shaft 302, and proximally beyond the handle 314. Additionally, the distal end 310 of the guide shaft 302 includes a curved tip region 312 that can guide the flexible element 306 to a selected position and orientation, as described above with respect to the microfracture device 100 shown in FIGS. 1A and 1B. In some implementations, the microfracture device 300 can include a handle 314 coupled to, or formed integral with, the proximal end 308 of the guide shaft 302 to control the movement of the guide shaft 302 relative to the stabilizing portion 304 and the surgical site.

The stabilizing portion 304 includes a body 316 and a portion of the body 316 that can receive the guide shaft 302. For example, an internal passage (not shown) through the body 316 can receive at least a portion of the guide shaft 302 such that the guide shaft 302 can slide and/or rotate relative to the body 316. Additionally, the body 316 can include a flexible wide portion 318 having a conforming outer surface 320. The conforming outer surface 320 can be substantially curved or contoured such that it generally conforms to a contacting bone surface, for example, a portion of a femoral head (FIG. 2A). In some cases, the flexible wide portion 318 can be loosely fitted with respect to the guide shaft 302 such that the flexible wide portion 318 can tilt in all directions relative to the guide shaft 302. Such tilting motion can help enhance a conformability of the conforming outer surface 320 by first generally tangentially orienting the outer surface 320 relative to the contacting bone surface. Additionally, or alternatively, the body 316 can define a cutout 322 such that additional constraints to the relative tilting motion of the flexible wide portion 318 are reduced.

The flexible wide portion 318 and the body 316 of the stabilizing portion 304 can be made from a single piece of material, or may be formed separately and attached to each other. The flexible wide portion 318 can be made from any flexible or elastic material, such as an elastomer. The body 316 can be made from any biocompatible material including elastomers and other polymers, metals, ceramics, or combinations thereof. In some cases, the flexible wide portion 318 may be coupled directly to the guide shaft 302 via, for example, an adhesive or a press fit.

Figure 4:
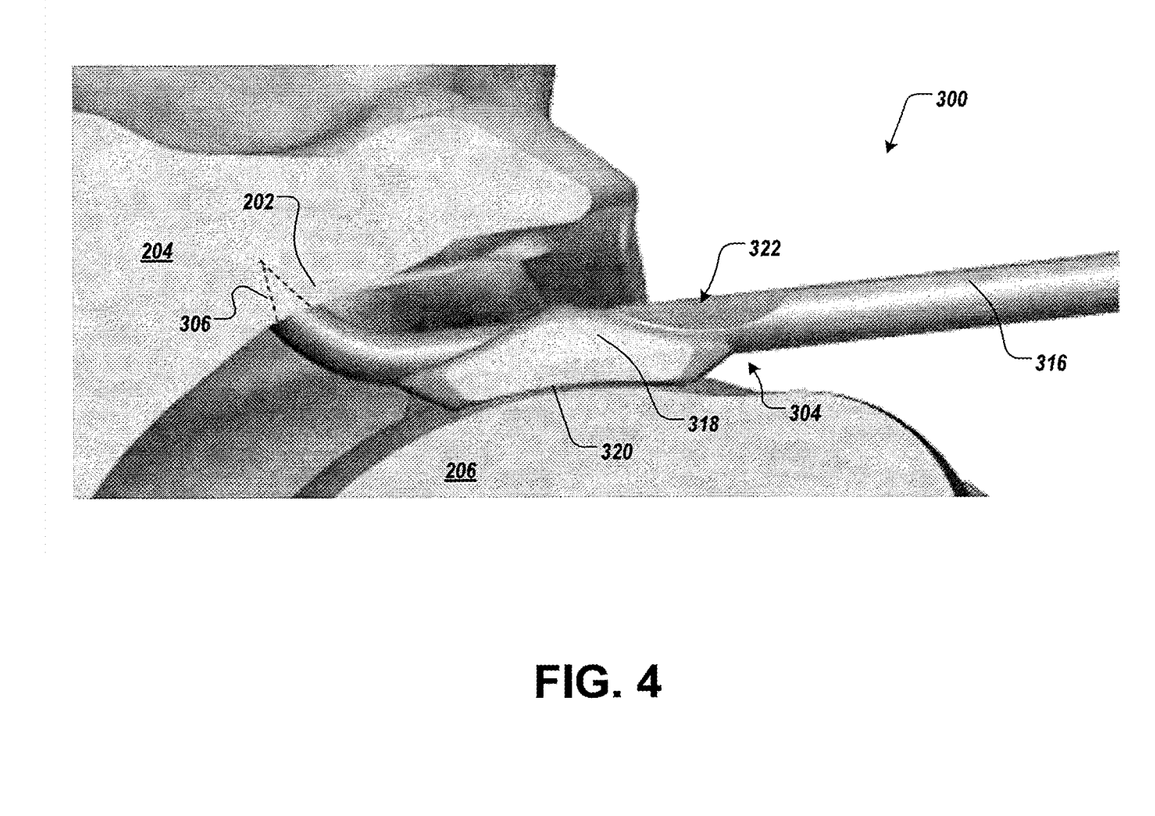
FIG. 4 illustrates positioning and use of the microfracture device of FIGS. 3A and 3B within the acetabular region for performing a microfracture procedure.

Referring now to FIG. 4, during a microfracture procedure, the microfracture device 300 may be used as described above with respect to FIGS. 2A and 2B to create microfracture channels, such as channel 306, in the subchondral bone of, for example, the acetabular cup 204. Additionally, in use, the surgeon can position the flexible wide portion 318 on the outer surface of the femoral head 206 such that the enhanced conformability between the conforming outer surface 320 and the outer surface of the femoral head 206 provides additional stability before and during the channel drilling process.

Figure 5:
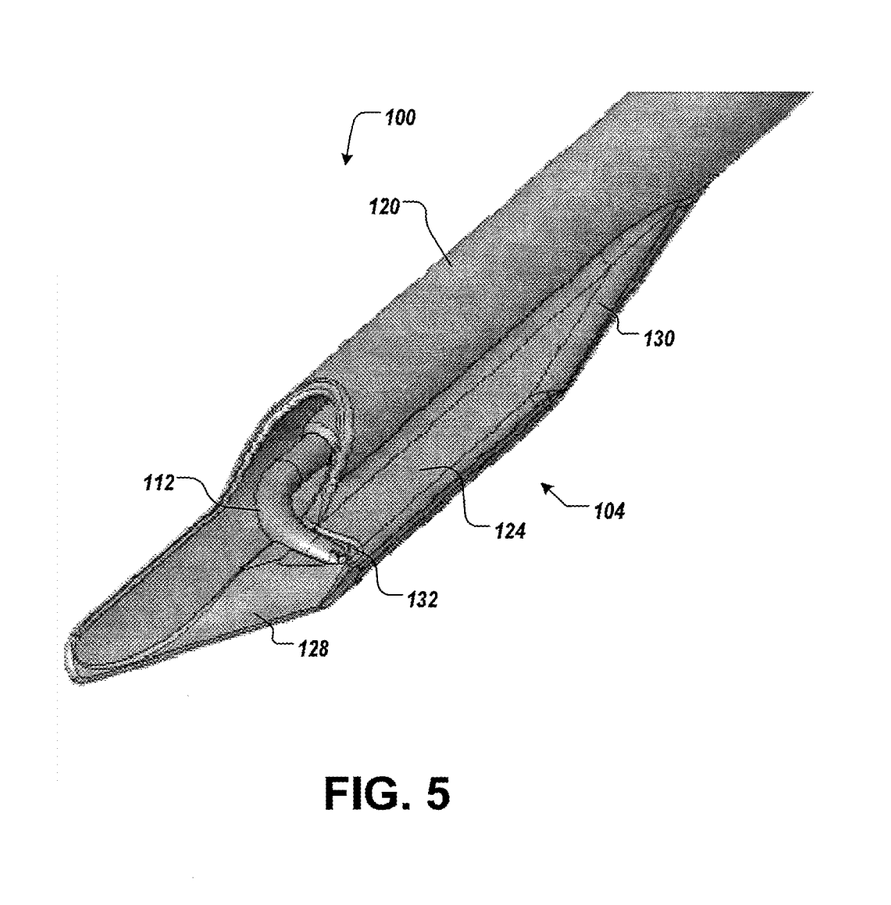
FIG. 5 is a partial perspective view of the microfracture device of FIG. 1A in a retracted position.

Referring to FIG. 5, the guide shaft 102 of the microfracture device 100 is shown in a retracted position for use during, for example, insertion into and removal from the microfracture site. In the retracted position, the microfracture device 100 has a reduced cross-sectional area such that it can fit down, for example, a relatively thinner arthroscopic cannula and not snag on soft tissue. Additionally, or alternatively, the leading edge 128 and the trailing edge 130 reduces the likelihood of the wide portion 124 getting snagged on, for example, soft tissue.

Figure 6:
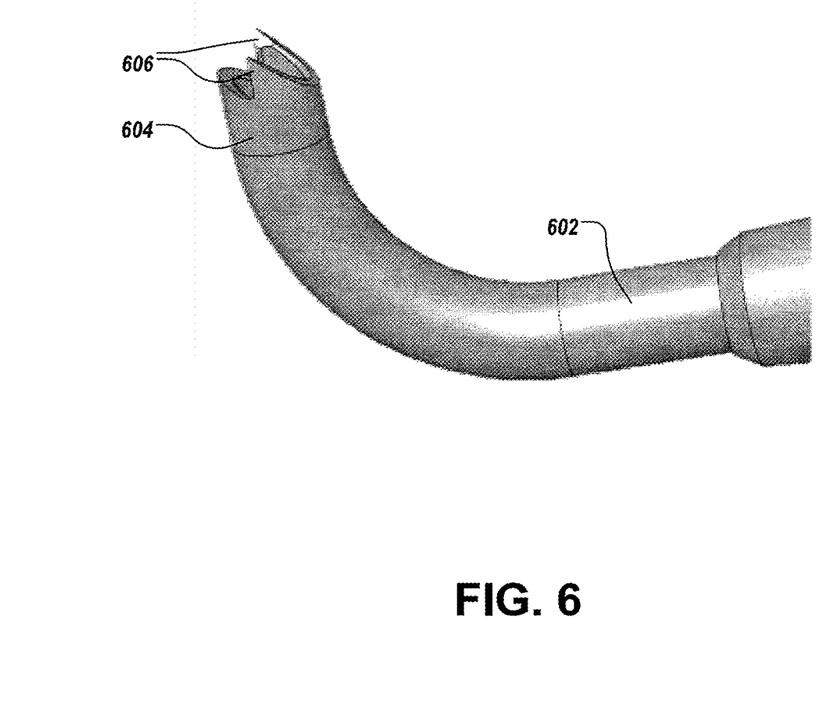
FIG. 6 is a perspective view of an angled distal tip for use in a microfracture device.
Figure 7A:
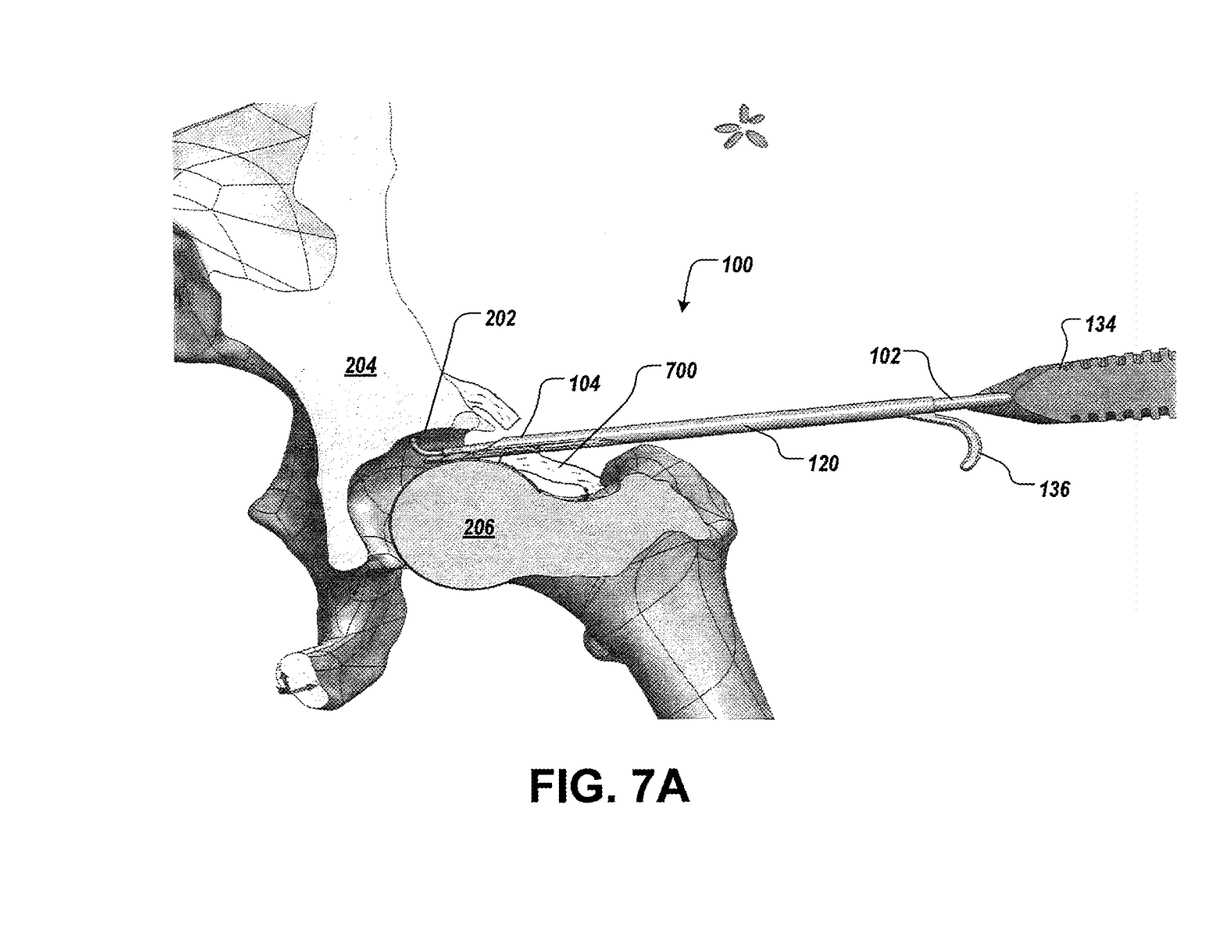
FIGS. 7A and 7B illustrate alternative positioning and use of the microfracture device of FIG. 1A within an acetabular region.
Figure 7B:
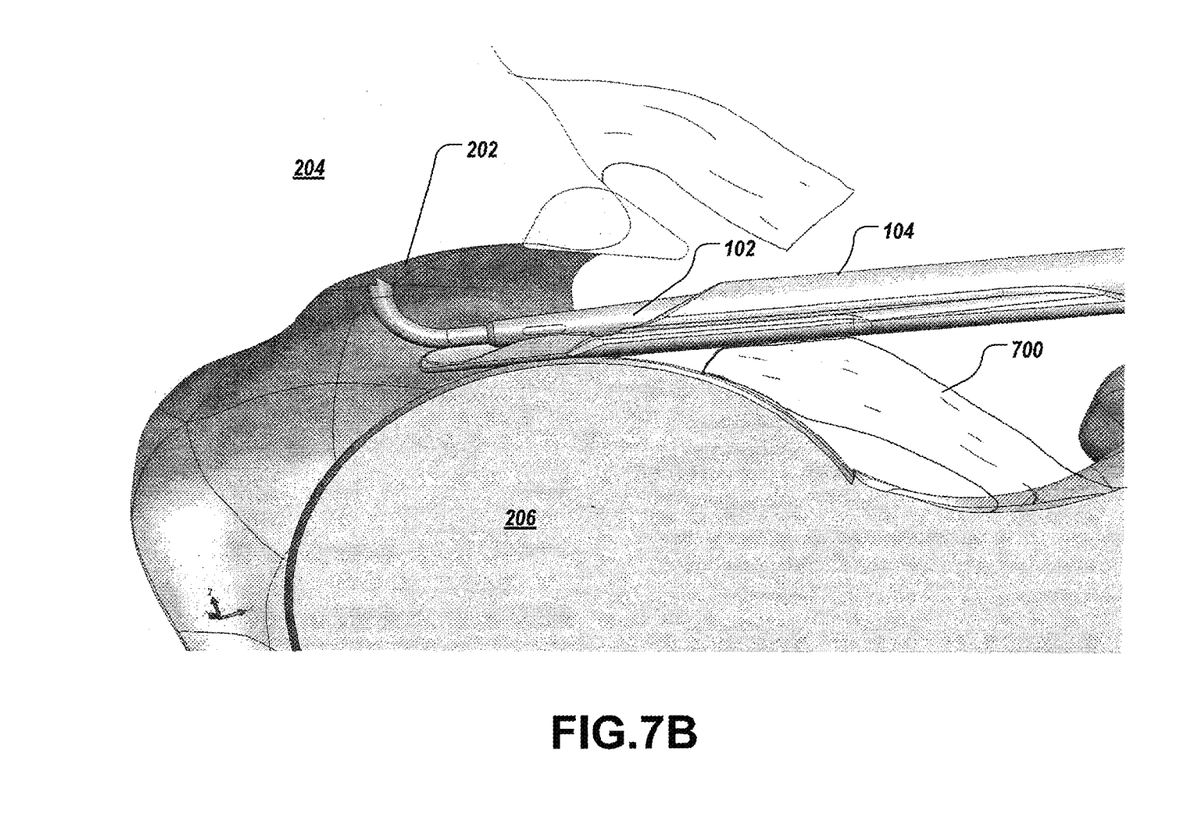

Referring to FIG. 6, an angled distal tip 604 of a guide shaft 602 includes one or more teeth 606 for driving into subchondral bone tissue, such as the acetabular cup 204 (FIG. 2A). In use, the surgeon can locate the distal tip 604 at the microfracture site 202 (FIG. 2A) and embed at least a portion or all of the teeth 606 into the surface of the bone. The teeth 606 can help minimize, for example, unseating of the distal tip 604 from the bone surface and/or skiving or dragging of the distal tip 604 across the bone surface as the flexible element is driven into the subchondral bone tissue to form the microfracture channels.

Figure 8:
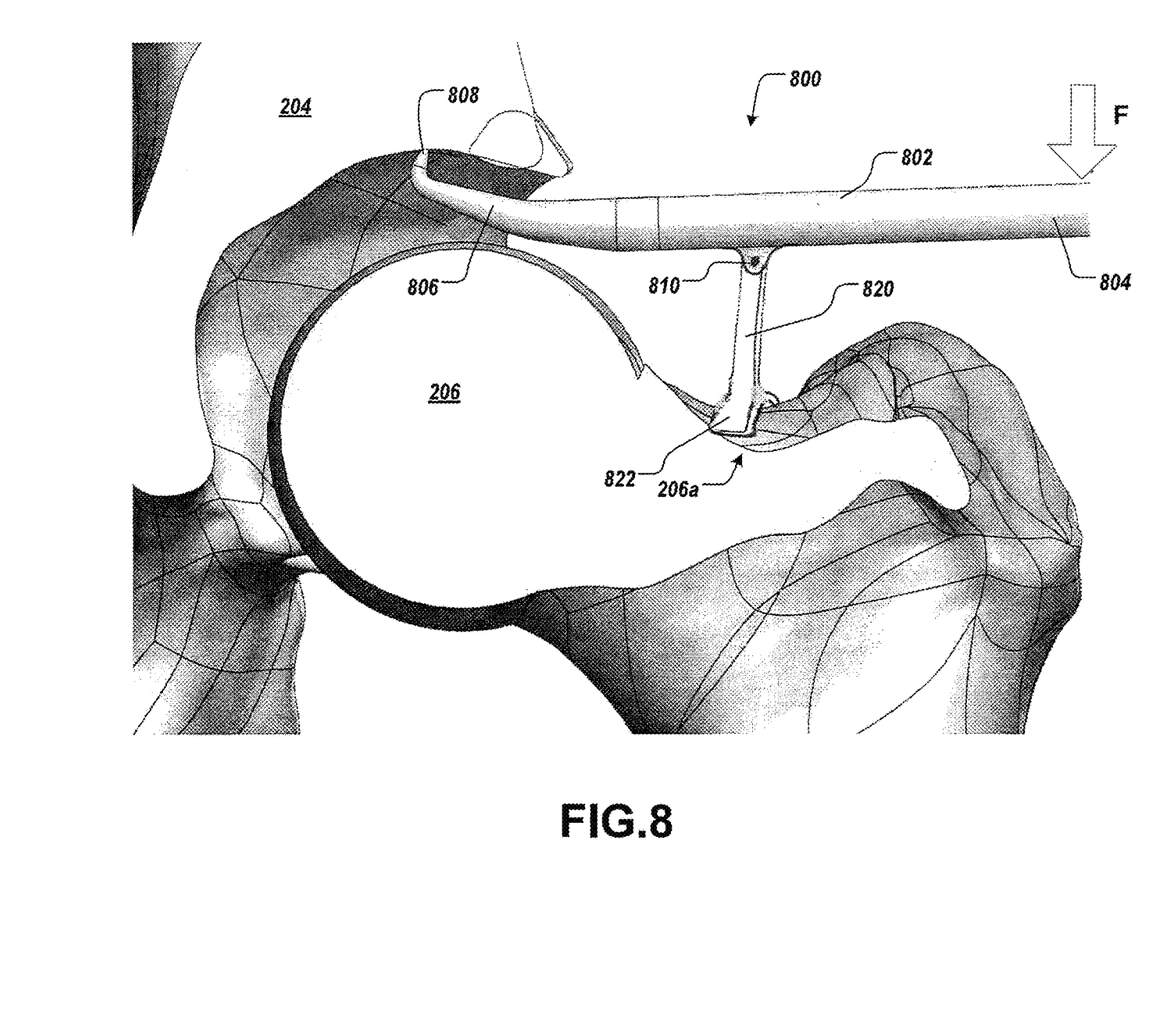
FIG. 8 illustrates a side view of an alternative implementation of a microfracture device.

Referring to FIG. 8, in an alternative implementation, a microfracture device 800 includes a microfracture pick 802 having a proximal end 804 and a distal end 806. The pick 802 has a sharp bent tip 808 located on its distal end 806. The pick 802 includes a hinge or bracket 810 located between its proximal end 804 and its distal end 806. A support bracket or post 820 is rotationally or pivotally mounted to the hinge 810 such that it can be rotated to a position proximate the pick 802 or through a number of angular positions relative to the pick 802. In some implementations, the bracket 820 can be rotated through an arc of approximately 180 degrees relative to the pick 802.

In use, a surgeon delivers the pick 802 and rotatably connected bracket 820 through, for example, a standard slotted arthroscopic cannula, to a desired location, such as an underside of an acetabular cup 204 as shown in FIG. 8, and places the tip 808 at the desired location for making a channel within the subchondral bone. In order to deliver the required force for driving the tip 808 into the subchondral bone, the surgeon can position a portion of the bracket 810, for example, a curved or semi-cylindrical portion 822 of the bracket 810 onto a portion of a bone surface, such as a portion of a femoral neck 206a. Once in the desired position, the surgeon can apply a downward force (denoted by arrow F in FIG. 8) to the proximal end 804 of the pick 802. The applied downward force causes the distal end 806 of the pick 802 to rotate about the support bracket 820 such that the sharp tip 808 is driven into the subchondral bone at the desired location. Utilizing the support bracket 820 of the present implementation avoids contact with the overlying cartilage or other soft tissues of the femoral head.

Figure 9:
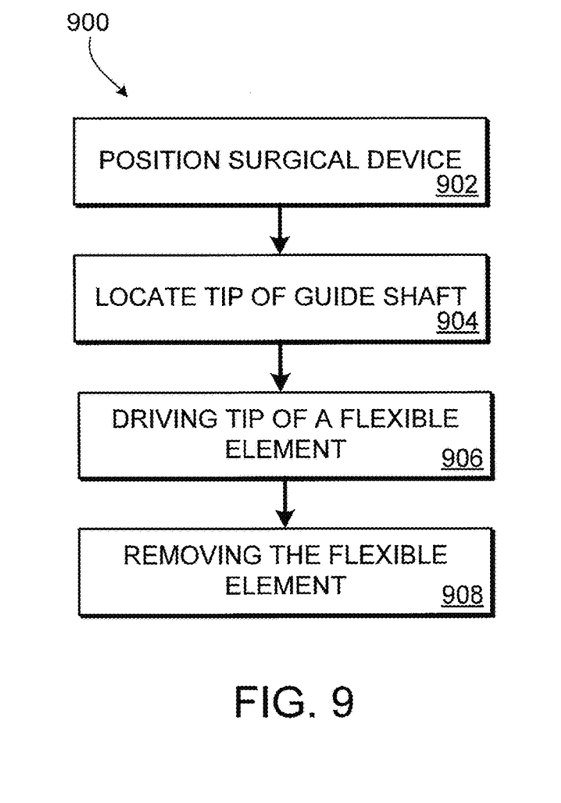
FIG. 9 illustrates a method of microfracture stimulation of the present disclosure.

Referring to FIG. 9, the present disclosure further includes a method of performing a procedure such as microfracture stimulation 900. The process 900 includes positioning a surgical device having a guide shaft with a proximal end and a distal end and an angled tip at the distal end and a stabilizing portion disposed along an outer surface of the guide shaft proximate to a first bone surface such that an outer surface of the stabilizing portion is positioned against a portion of the first bone surface 902. The positioning step 902 may include inserting at least a portion of the surgical device into a standard arthroscopic cannula. The first bone surface can include a portion of a femoral head. The stabilizing portion can include an outer surface having one of a substantially flat portion or a substantially curved portion and the positioning step 902 includes positioning one of the substantially flat or curved portions against the portion of the femoral head.

The process 900 also includes locating the angled tip of the guide shaft at a desired point of stimulation 904. Step 904 may include insertion of at least a portion of the guide shaft into a standard arthroscopic cannula.

The process 900 includes driving an angled tip of a flexible element through the guide shaft and into a second bone surface 906. The second bone surface can include a portion of the acetabulum. The process 900 includes removing the flexible element 908, thereby leaving a small channel in the underlying subchondral bone. Eventually, blood will travel in the channel to form fibrous cartilage.

While this document contains many specific implementation details, these should not be construed as limitations on the scope of any implementations or of what may be claimed, but rather as descriptions of features specific to particular implementations. For example, the guide shafts 102, 302 may include additional bends and curves for improved positioning of the distal ends 110, 310, or to permit avoidance of certain structures such as the greater trochanter. In other implementations, the guide shafts 102, 302 may be a solid shaft designed to dig into the microfracture site 202 upon application of a downward force at the proximal end 108, 308. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, while particular implementations of the subject matter have been described, other implementations are within the scope of the following claims.

What is claimed is:

1. A microfracture device comprising:
   a guide shaft having a proximal end and a distal end and defining an internal passage between the proximal and distal ends, the distal end having a curved tip;
   a stabilizing portion disposed along an outer surface of the guide shaft, at least a portion of the stabilizing portion being wider than the guide shaft; and
   a flexible element movably positioned within the internal passage of the guide shaft, the flexible element having a distal tip configured for driving into bone;
   wherein the stabilizing portion includes a recessed portion for receiving a portion of the curved tip of the distal end of the guide shaft; and
   wherein the stabilizing portion comprises a flexible body having at least one substantially curved outer surface.

2. The device of claim 1, further comprising a handle operatively coupled to the proximal end of the guide shaft.

3. The device of claim 2, wherein the handle defines a passageway configured to receive a portion of the flexible element therethrough.

4. The device of claim 2, wherein the handle is operatively coupled to the proximal end of the guide shaft such that the guide shaft can be translated proximally and distally relative to the stabilizing portion and rotated relative to the stabilizing portion.

5. The device of claim 1, wherein the guide shaft comprises at least one angled tooth at the distal end of the guide shaft.

6. The device of claim 1, wherein the body defines an internal passage that receives a portion of the guide shaft therethrough.

7. The device of claim 6, wherein the body defines a longitudinally extending slit that permits the guide shaft to be disposed in and removed from the internal passage of the body.

8. The device of claim 1, wherein the flexible element comprises a proximal end that is operatively configured to permit translation of the flexible element proximally and distally through the internal passage of the guide shaft.

9. The device of claim 8, wherein the proximal end of the flexible element is further operatively configured to permit rotation of the flexible element within the internal passage of the guide shaft.

10. The device of claim 1, wherein the flexible element comprises a flexible wire.

11. A method of performing a microfracture procedure comprising:
    positioning a surgical device having a guide shaft with a proximal end and a distal end and an angled tip at the distal end and a stabilizing portion disposed along an outer surface of the guide shaft proximate to a first bone surface such that an outer surface of the stabilizing portion is positioned against a portion of the first bone surface;
    locating the angled tip of the guide shaft at a desired point of stimulation;
    driving an angled tip of a flexible element through the guide shaft and into a second bone surface; and
    removing the flexible element;
    wherein the flexible element comprises a flexible wire, and wherein driving the angled tip of the flexible wire comprises striking a proximal end of the flexible wire to translate the flexible wire relative to the guide shaft.

12. The method of claim 11, further comprising engaging the angled tip of the guide shaft into the second bone surface.

13. The method of claim 11, wherein the first bone surface comprises a portion of a femoral head and the second bone surface comprises a portion of an acetabulum.

14. The method of claim 13, wherein the stabilizing portion comprises an outer surface having one of a substantially flat portion or a substantially curved portion and the positioning step comprises positioning one of the substantially flat or curved portions against the portion of the femoral head.

15. The method of claim 11, wherein the positioning step includes the step of inserting at least a portion of the surgical device into an arthroscopic cannula.

* * * * *